United States Patent
Skurnik et al.

(10) Patent No.: US 11,624,051 B2
(45) Date of Patent: Apr. 11, 2023

(54) COMPOSITION OR MATRIX FOR STORAGE OF BACTERIOPHAGES COMPRISING NANOFIBRILLAR CELLULOSE

(71) Applicant: UPM-KYMMENE CORPORATION, Helsinki (FI)

(72) Inventors: Mikael Skurnik, Masala (FI); Saija Kiljunen, Raisio (FI); Sheetal Patpatia, Vantaa (FI); Markus Nuopponen, Helsinki (FI); Lauri Paasonen, Järvenpää (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

(21) Appl. No.: 16/552,955

(22) Filed: Aug. 27, 2019

(65) Prior Publication Data
US 2020/0071659 A1 Mar. 5, 2020

(30) Foreign Application Priority Data
Aug. 28, 2018 (EP) .................................... 18191194

(51) Int. Cl.
*C12N 1/04* (2006.01)
*A61L 15/36* (2006.01)
*C12N 7/00* (2006.01)
*B82Y 5/00* (2011.01)
*A61L 15/32* (2006.01)
*C12N 5/00* (2006.01)

(52) U.S. Cl.
CPC .............. *C12N 1/04* (2013.01); *A61L 15/325* (2013.01); *A61L 15/36* (2013.01); *C12N 7/00* (2013.01); *B82Y 5/00* (2013.01); *C12N 5/0012* (2013.01); *C12N 2795/00011* (2013.01)

(58) Field of Classification Search
None
See application file for complete search history.

(56) References Cited

U.S. PATENT DOCUMENTS

| | | | |
|---|---|---|---|
| 6,202,946 B1 | 3/2001 | Virtanen | |
| 2018/0119235 A1 | 5/2018 | Talianski et al. | |

FOREIGN PATENT DOCUMENTS

| | | | |
|---|---|---|---|
| EP | 3335695 A1 | 6/2018 | |
| JP | 2013-541956 A | 11/2013 | |
| JP | 2018-519791 A | 7/2018 | |
| WO | 2003/093462 A2 | 11/2003 | |
| WO | 2006/047872 A1 | 5/2006 | |
| WO | 2012/056111 A2 | 5/2012 | |
| WO | 2012/094407 A1 | 7/2012 | |
| WO | 2012/175749 A1 | 12/2012 | |
| WO | 2013072563 A1 | 5/2013 | |
| WO | 2016/156878 A1 | 10/2016 | |
| WO | WO-2016156878 A1 * | 10/2016 | ............. C04B 28/02 |
| WO | 2017174874 A1 | 10/2017 | |

OTHER PUBLICATIONS

Lovalenti et al., Pharm Res, 2016, 33:1144-1160. (Year: 2016).*
Khalil et al., Carbohydrate Polymers, 2014, 99:649-665. (Year: 2014).*
European Search Report from European Patent Application No. EP 18191194.2, dated Oct. 22, 2018 (11 pages).
Extended European Search Report from European Patent Application No. EP 18191194.2, dated Jan. 14, 2019 (12 pages).
Nogueira et al., "Immobilization of bacteriophage in wound-dressing nanostructure," Nanomedicine: Nanotechnology, Biology and Medicine, vol. 13, No. 8, dated Aug. 8, 2017 (Aug. 8, 2017), pp. 2475-2484, XP085257007, ISSN: 1549-9634, DOI: 10.1016/J. Nano.
Hoefer et al., "A Novel In Situ Self-Dissolving Needle Web Based on Medicated Cellulose Hollow Fibres with Drug Delivery Features," The Open Medical Devices Journal, vol. 3, No. 1, Dec. 29, 2011 (Dec. 29, 2011), pp. 1-8, XP55060738, ISSN: 1875-1814, DOI: 10.2174/1875181401103010001.
Sanati et al., "Improved procedure for screening expression libraries for novel autoantigens," Iranian Journal of Biotechnology, vol. 1, No. 1, Jan. 1, 2003 (Jan. 1, 2003), pp. 31-35, XP55538310.
Chinga-Carrasco, "Cellulose fibres, nanofibrils and microfibrils: The morphological sequence of MFC components from a plant physiology and fibre technology point of view," Nanoscale Research Letters, vol. 6, No. 1, Jan. 1, 2011 (Jan. 1, 2011), p. 417, XP55021830, ISSN: 1556-276X, DOI: 10.1186/1556-276X-6-417.
Hongyang et al., "Nanofibrous Microfiltration Membrane Based on Cellulose Nanowhiskers," Biomacromolecules, vol. 13, No. 1, Jan. 9, 2012 (Jan. 9, 2012), pp. 180-186, XP55513573, US ISSN: 1525-7797, DOI: 10.1021/bm201421g.
Hongyang et al., "Ultrafine Polysaccharide Nanofibrous Membranes for Water Purification," Biomacromolecules, vol. 12, No. 4, Apr. 11, 2011 (Apr. 11, 2011), pp. 970-976, XP55513664, US ISSN: 1525-7797, DOI: 10.1021/bm1013316.
Notice of Reasons for Rejection in Japanese Patent Application No. JP 2019-152284, dated Jan. 6, 2022 (2 pages w/English translation).
Vonasek, E. et al., "Bacteriophages immobilized on electrospun cellulose microfibers by non-specific adsorption, protein-ligan binding, and electrostatic interactions," Cellulose 24, pp. 4581-4580, 2017.
Notice of Reasons for Rejection in Japanese Patent Application No. JP 2019-152284, dated May 24, 2022 (3 pages w/English translation).
Serizawa T. et al., "Hydrolytic Activities of Crystalline Cellulose Nanofibers," Biomacromolecules 14 pp. 613-617, 2013.

* cited by examiner

*Primary Examiner* — Nicole Kinsey White
(74) *Attorney, Agent, or Firm* — Nixon Peabody LLP

(57) ABSTRACT

A composition or matrix comprising a bacteriophage and nanofibrillar cellulose or a derivative thereof in a wet or dry state is disclosed.

11 Claims, 9 Drawing Sheets

COMPOSITION OR MATRIX FOR STORAGE OF BACTERIOPHAGES COMPRISING NANOFIBRILLAR CELLULOSE

CROSS-REFERENCE TO RELATED APPLICATIONS

This application claims the benefit of European Patent Application No. 18191194.2, filed Aug. 28, 2018, which is hereby incorporated by reference in its entirety.

TECHNICAL FIELD

The present disclosure relates to a composition or matrix, to an arrangement, to methods and to the use of the composition or matrix.

BACKGROUND

There is growing interest in bacteriophages as objects of research and potential agents for biological control. For example, the use of bacteriophages is an emerging therapy area that is intended to replace or supplement the use of antibiotics. Effective bacteriophage treatment requires the use of a suitable bacteriophage that is capable of infecting the target bacterial strain. Bacteriophage libraries may be used for screening suitable bacteriophages.

For such uses, it is important to be able to store bacteriophages even for prolonged time periods while maintaining their viability and to transport, i.e. ship, them from one location to another. Bacteriophages should survive and remain viable during the storage and shipping.

SM buffer including sodium chloride, magnesium sulfate, Tris and gelatin has been used for storage of bacteriophages. There is a need for improved methods for storing, maintaining and delivering bacteriophages, even for prolonged time periods.

SUMMARY

A composition or matrix comprising a bacteriophage and nanofibrillar cellulose or a derivative thereof in a wet or dry state is disclosed.

BRIEF DESCRIPTION OF THE DRAWINGS

The accompanying drawings, which are included to provide a further understanding of the embodiments and constitute a part of this specification, illustrate various embodiments. In the drawings.

DETAILED DESCRIPTION

Figure 1:
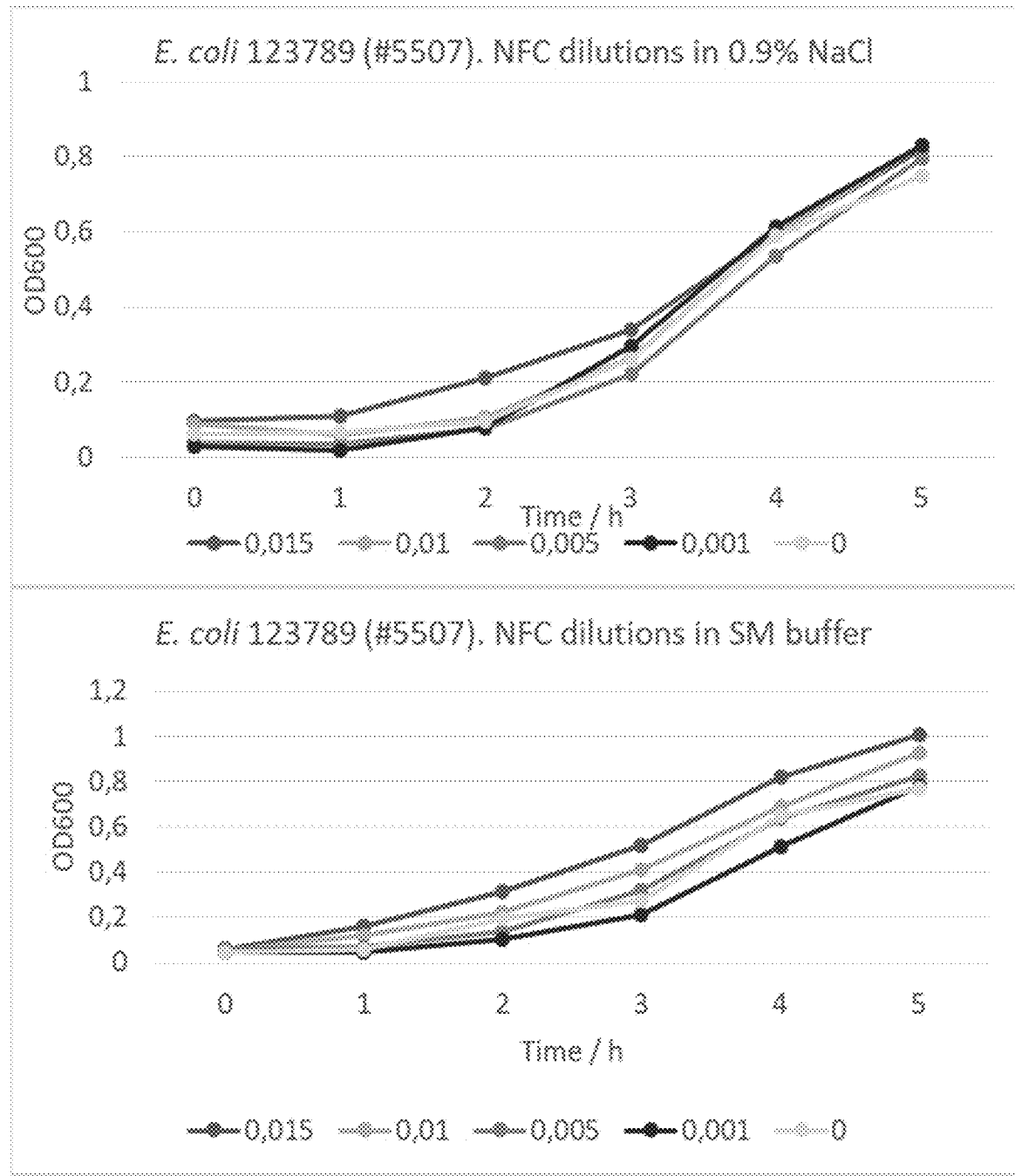
FIG. 1 shows exemplary results for *E. coli* 123789 (#5507) growth in the presence of GROWDEX® hydrogel from UPM-Kymmene Corporation, Helsinki, Finland.

A composition or matrix comprising a bacteriophage and nanofibrillar cellulose or a derivative thereof in a wet or dry state is disclosed.

The presence of the nanofibrillar cellulose or a derivative thereof appears to allow for storing various bacteriophages, even for a prolonged time. It may thus be possible to e.g. store and ship bacteriophages from a central phage library laboratory to clinical laboratories for screening and therapy purposes.

The handling of the composition or matrix is also relatively easy, and the risk for contamination and cross-contamination may be reduced, for example when compositions or matrices are handled, stored or transported.

The composition or matrix and the methods may be suitable for various different types of bacteriophages.

Furthermore, the composition or matrix may be used to deliver bacteriophages to a subject for medical and therapeutical purposes. The composition or matrix may be based on plant-derived material or material derived from a microorganism, so it does not necessarily have to contain anything derivable from animals.

The composition or matrix have been found to work significantly better than e.g. certain other gel-like materials, such as hydrogels containing sodium carboxymethylcellulose and other components, such as calcium alginate or propylene glycol.

The nanofibrillar cellulose does not appear to have a significant effect on the growth of bacteria on or in the composition or matrix. Thus the composition or matrix may be used as a medium to which prokaryotic cells, such as bacteria, for example in the form of a prokaryotic cell suspension, such as bacterial suspension, is added and subsequently allowed to grow and/or multiply. By observing the growth of the prokaryotic cells on or in the composition or matrix it may be possible to determine whether the bacteriophage is capable of infecting the prokaryotic cells.

The terms "bacteriophage" and "phage" may be used interchangeably. They may refer to a virus that is capable of infecting prokaryotic cells, i.e. bacteria and/or archaea. Bacteriophages may vary in shape and genetic material. For example, a bacteriophage may have a capsid that is icosahedral, octahedral or filamentous. A bacteriophage may also have a head-tail structure, comprising e.g. an icosahedral capsid (head), a tail and optionally other parts, such as a collar. The term "a bacteriophage" or "the bacteriophage" may refer to one or more species of bacteriophages, and/or to one or more bacteriophage particles.

In the context of this specification, the prokaryotic cells may comprise or be bacteria and/or archaea. The prokaryotic cells may be selected such that they are capable of functioning as host cells for the bacteriophage.

Examples of bacteriophages, for which the present composition or matrix may be suitable, include the order Caudovirales (including the families Myoviridae, Siphoviridae, Podoviridae) and Ligamenvirales (Lipothrixviridae, Rudiviridae); and families Ampullaviridae, Bicaudaviridae, Clavaviridae, Corticoviridae, Cystoviridae, Fuselloviridae, Globuloviridae, Guttaviridae, Inoviridae, Leviviridae, Microviridae, Plasmaviridae, and/or Tectiviridae. The composition or matrix, the methods and the uses are not particularly limited to any order, family or species of bacteriophages. However, they may be better suited for some bacteriophages than for others.

A bacteriophage may be considered to be viable, if it is capable of infecting prokaryotic cells and subsequently multiplying in them. The viability of bacteriophages may be tested e.g. as described in the examples.

The nanofibrillar cellulose may be prepared from cellulose raw material of a plant origin. The raw material may be based on any plant material that contains cellulose. The plant material may be, for example, wood. The wood may be from a softwood tree, such as spruce, pine, fir, larch, Douglas fir or hemlock, or from a hardwood tree, such as birch, aspen, poplar, alder, eucalyptus, oak, beech or acacia, or from a mixture of a softwood and a hardwood. In an embodiment, the nanofibrillar cellulose is obtained from wood pulp. In an embodiment, the nanofibrillar cellulose is obtained from hardwood pulp. In an example, the hardwood is birch. In an embodiment, the nanofibrillar cellulose is obtained from softwood pulp.

The nanofibrillar cellulose may be made of plant material. In an example, the fibrils are obtained from non-parenchymal plant material. In such a case, the fibrils may be obtained from secondary cell walls. One abundant source of such cellulose fibrils is wood fibres. The smallest cellulosic entities of cellulose pulp of plant origin, such as wood, include cellulose molecules, elementary fibrils, and microfibrils. Microfibril units are bundles of elementary fibrils caused by physically conditioned coalescence as a mechanism of reducing the free energy of the surfaces.

The nanofibrillar cellulose may be manufactured by homogenizing wood-derived fibrous raw material, which may be chemical pulp. Cellulose fibers may be disintegrated to produce fibrils which have a diameter in the nanometer range, which diameter may be up to 200 nm, or up to 50 nm, for example in the range of 1-200 nm or 1-100 nm, and gives a dispersion of fibrils in water. The fibrils may be reduced to a size in which the diameter of most of the fibrils is in the range of 2-20 nm. The fibrils originating from secondary cell walls may be essentially crystalline, with a degree of crystallinity of at least 55%. Such fibrils may have different properties than fibrils originated from primary cell walls; for example, the dewatering of fibrils originating from secondary cell walls may be more challenging.

In the context of this specification, the term "nanofibrillar cellulose" may refer to cellulose fibrils or fibril bundles separated from cellulose-based fiber raw material. These fibrils are characterized by a high aspect ratio (length/diameter): their length may exceed 1 μm, whereas the diameter typically remains smaller than 200 nm. The smallest fibrils are in the scale of so-called elementary fibrils, their diameter being typically in the range of 2-12 nm. The dimensions and size distribution of the fibrils may depend on the refining method and efficiency. Nanofibrillar cellulose may be characterized as a cellulose-based material, in which the median length of particles (fibrils or fibril bundles) is not greater than 50 μm, for example in the range of 1-50 μm, and the particle diameter is smaller than 1 μm, for example in the range of 2-500 nm. In case of native nanofibrillar cellulose, in an embodiment the average diameter of a fibril is in the range of 5-100 nm, for example in the range of 10-50 nm. Intact, unfibrillated microfibril units may be present in the nanofibrillar cellulose. In the context of this specification, the term "nanofibrillar cellulose" is not meant to encompass non-fibrillar, rod-shaped cellulose nanocrystals or whiskers.

The nomenclature relating to nanofibrillar cellulose is currently not uniform, and terms may be inconsistently used in the literature. For example, the following terms may have been used as synonyms for nanofibrillar cellulose: cellulose nanofiber (CNF), nanofibril cellulose, nanofibrillated cellulose (NFC), nanocellulose, nano-scale fibrillated cellulose, microfibrillar cellulose, cellulose microfibrils, microfibrillated cellulose (MFC), and fibril cellulose.

Nanofibrillar cellulose is characterized by a large specific surface area and a strong ability to form hydrogen bonds. In a water dispersion, the nanofibrillar cellulose typically appears as either a light or turbid gel-like material. Depending on the fiber raw material, nanofibrillar cellulose may also contain small amounts of other wood components, such as hemicellulose or lignin. The amount is dependent on the plant source.

Different grades of nanofibrillar cellulose may be categorized based on three main properties: (i) size distribution, length and diameter; (ii) chemical composition; and (iii) rheological properties. To fully describe a grade, the properties may be used in parallel. Examples of different grades may include native (or non-modified) NFC, oxidized NFC (high viscosity), oxidized NFC (low viscosity), carboxymethylated NFC and cationized NFC. Within these main grades, also sub-grades may exist, for example: extremely well fibrillated vs. moderately fibrillated, high degree of substitution vs. low, low viscosity vs. high viscosity, etc. The fibrillation technique and the chemical pre-modification may have an influence on the fibril size distribution. Typically, non-ionic grades may have a wider fibril diameter (for example in the range of 10-100 nm, or 10-50 nm), while the chemically modified grades may be thinner (for example in the range of 2-20 nm). The distributions of the fibril dimensions may be also narrower for the modified grades. Certain modifications, especially TEMPO oxidation, may yield shorter fibrils.

In the context of this specification, the term "nanofibrillar cellulose" may also be understood as referring to a derivative of nanofibrillar cellulose.

Depending on the raw material source, e.g. hardwood (HW) vs. softwood (SW) pulp, different polysaccharide compositions may be present in the final nanofibrillar cellulose product. Commonly, non-ionic grades are prepared from bleached birch pulp, which may yield a high xylene content (25% by weight). Modified grades may be prepared either from HW or SW pulps. In such modified grades, the hemicelluloses may also be modified together with the cellulose domain. The modification may not be homogeneous, i.e. some parts may be modified to a greater extent than others. Thus, a detailed chemical analysis may not be possible—the modified products are typically complex mixtures of different polysaccharide structures.

The dimensions of the fibrils or fibril bundles may be dependent on the raw material and the disintegration method. Mechanical disintegration of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegration treatment may be performed at conditions in which water is sufficiently present to prevent the formation of bonds between the fibers.

In an example, the disintegration is carried out by using a disperser having at least one rotor, blade or similar moving mechanical member, such as a rotor-rotor dispergator. One example of a rotor-rotor dispergator is an Atrex device.

Another example of a device suitable for disintegrating is a pin mill, such as a multi-peripheral pin mill. One example of such device is described in U.S. Pat. No. 6,202,946 B1.

In an embodiment, the disintegrating is carried out by using a homogenizer.

In the context of this specification, the term "fibrillation" may generally refer to disintegrating fiber material mechanically by work applied to the particles, whereby cellulose fibrils are detached from the fibers or fiber fragments. The work may be based on various effects, such as grinding, crushing or shearing, or a combination of these, or another corresponding action that reduces the particle size. The energy taken by the refining work may normally be expressed in terms of energy per processed raw material quantity, in units of e.g. kWh/kg, MWh/ton, or units proportional to these. The expressions "disintegration" or "disintegration treatment" may be used interchangeably with "fibrillation". The fiber material dispersion that is subjected to fibrillation may be a mixture of fiber material and water (or an aqueous solution), also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

In an aqueous environment, a dispersion of nanofibrillar cellulose or a derivative thereof may form a viscoelastic hydrogel network. The gel may be formed at relatively low concentrations of, for example, 0.05-0.2% (w/w), dispersed and hydrated entangled fibrils. The viscoelasticity of the NFC hydrogel may be characterized, for example, by dynamic oscillatory rheological measurements. Nanofibrillar cellulose hydrogels may exhibit characteristic rheological properties. For example, they are shear-thinning or pseudoplastic materials, which means that their viscosity depends on the speed (or force) by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity can be seen after exceeding the critical shear stress. The zero shear viscosity and the yield stress may be the most important rheological parameters to describe the suspending power of the materials. These two parameters may separate the different grades quite clearly and thus may enable classification of the grades.

Nanofibrillar cellulose may also be characterized by the average diameter (or width), or by the average diameter together with the viscosity, such as Brookfield viscosity or zero shear viscosity. In an embodiment, the nanofibrillar cellulose has a number average diameter of a fibril in the range of 1-100 nm. In an embodiment, the nanofibrillar cellulose has a number average diameter of a fibril in the range of 1-50 nm. In an embodiment, said nanofibrillar cellulose has a number average diameter of a fibril in the range of 2-15 nm, such as TEMPO oxidized nanofibrillar cellulose. The diameter of a fibril may be determined using several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general, AFM and TEM may be well suited for nanofibrillar cellulose grades with narrow fibril diameter distribution.

The viscosity of the nanofibrillar cellulose may be measured using a rheometer. In an example, a rheometer viscosity of the nanofibrillar cellulose dispersion is measured at 22° C. with a stress controlled rotational rheometer (AR-G2, TA Instruments, UK) equipped with a narrow gap vane geometry (the vane having a diameter of 28 mm and a length of 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of 1000 s-1 is exceeded. This method may be used for determining the zero-shear viscosity.

In one example, the nanofibrillar cellulose, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium.

The nanofibrillar cellulose may have a storage modulus in the range of 0.3 to 50 Pa, when dispersed to a concentration of 0.5 w % in water. For example, the storage modulus may be in the range of 1 to 20 Pa, or in the range of 2 to 10 Pa, when dispersed to a concentration of 0.5 w % in water.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample. In a turbidity measurement method, a nanofibrillar cellulose sample may be diluted in water, to a concentration below the gel point of said nanofibrillar cellulose, and turbidity of the diluted sample may be measured. The concentration in which the turbidity of the nanofibrillar cellulose samples is measured may be 0.1%. HACH P2100 Turbidometer with a ml measuring vessel may be used for turbidity measurements. The dry matter of the nanofibrillar cellulose sample is determined and 0.5 g of the sample, calculated as dry matter, may be loaded in the measuring vessel, which may be filled with tap water to 500 g and vigorously mixed by shaking for about 30 s. Without delay the aqueous mixture may be divided into 5 measuring vessels, which are inserted in the turbidometer. Three measurements on each vessel may be carried out. The mean value and standard deviation may be calculated from the obtained results, and the final result may be given as NTU units.

One way to characterize nanofibrillar cellulose is to define both the viscosity and the turbidity. Low turbidity may correlate with a small size of the fibrils, such as small diameter, as small fibrils scatter light poorly. In general as the fibrillation degree increases, the viscosity increases and at the same time the turbidity decreases. This may happen, however, until a certain point. When the fibrillation is further continued, the fibrils may finally begin to break and cannot form a strong network any more. Therefore, after this point, both the turbidity and the viscosity may begin to decrease.

In an example, the turbidity of anionic nanofibrillar cellulose is lower than 90 NTU, for example from 3 to 90 NTU, such as from 5 to 60, for example 8-40, measured at a consistency of 0.1% (w/w) in aqueous medium, and measured by nephelometry. In an example the turbidity of native nanofibrillar cellulose may be even over 200 NTU, for example from 10 to 220 NTU, such as from 20 to 200, for example 50-200 measured at a consistency of 0.1% (w/w) in aqueous medium, and measured by nephelometry. To characterize the nanofibrillar cellulose, these ranges may be combined with the viscosity ranges of the nanofibrillar cellulose.

The starting material for the preparation of the composition or matrix may be nanofibrillar cellulose obtained or obtainable directly from the disintegration of some of the above-mentioned fibrous raw material and at a relatively low concentration homogeneously distributed in water due to the disintegration conditions. The starting material may be an aqueous gel at a concentration of 0.2-10% (w/w).

The composition or matrix may comprise from 0.1 to 99.9% (w/w) of the nanofibrillar cellulose or the derivative thereof. The consistency or nanofibrillar cellulose content of the composition or matrix may depend e.g. on whether it is in the wet or dry state. When in a dry state, the composition or matrix may comprise e.g. 96 to 98% (w/w) of nanofibrillar cellulose. The consistency or nanofibrillar cellulose content of the composition or matrix may, additionally or alternatively, depend on its intended use. For example, for transport purposes, a consistency of about 0.8% or higher, or about 1% or higher, may be well suited for a wet state, e.g. in the form of a hydrogel, or a dry state. Such a composition or matrix may have a sufficient viscosity such that it adheres well e.g. to a solid support.

In an embodiment, the composition or matrix is in a wet state. The term "wet state" may, in the context of this specification, refer to a state in which the composition or matrix comprises water and/or an aqueous solution, such that the nanofibrillar cellulose or the derivative thereof is mixed with or dispersed in the water or aqueous solution. For example, the composition or matrix may comprise more than 10% (w/w) of water and/or an aqueous solution. Alternatively or additionally, the composition or matrix may comprise more than 20% (w/w), or more than 30% (w/w), or more than 40% (w/w), or more than 50% (w/w), of water and/or an aqueous solution. The water/aqueous solution content may depend on the degree of wetting the composition or matrix for subsequent use and/or other conditions. The aqueous solution may be any aqueous solution compatible with the bacteriophage, for example a buffer solution or saline (NaCl solution). Examples of buffer solutions that are compatible with bacteriophages include SM buffer (100 mM NaCl, 10 mM $MgSO_4$, 50 mM Tris-HCl, pH 7.5, 0.002% (w/v) gelatin) and phage buffer (10 mM Tris-HCl, pH 7.5, 10 mM $MgCl_2$, 68 mM NaCl). For example, a bacteriophage in a buffer may be mixed or suspended with a nanofibrillar cellulose hydrogel, such that the resulting composition or matrix contains an amount of the buffer solution in addition to the water or aqueous solution derived from the nanofibrillar cellulose hydrogel. In an example, a bacteriophage in a buffer may be mixed or suspended with a nanofibrillar cellulose hydrogel at a volume ratio of 1:2 (i.e. 1 volume of phage in the buffer and 2 volumes of the hydrogel). In a further example, $Mg^{2+}$ ions may be included in the composition or matrix; it may enhance phage stability.

In the wet state, the consistency of the composition or matrix is not particularly limited. For example, consistencies in the range of 0.1 to 1.5% (w/w) are well suited, but higher consistencies may also be contemplated.

In the wet state, the nanofibrillar cellulose hydrogel or derivative thereof may be in the form of a dispersion. Thus the composition or matrix may be an aqueous dispersion of the nanofibrillar cellulose hydrogel or derivative thereof in water or an aqueous solution, and optionally comprising other ingredients.

As already mentioned, in an aqueous environment, a dispersion of nanofibrillar cellulose may form a viscoelastic hydrogel network. The composition or matrix may thus be in the form of a hydrogel. In such an embodiment, the bacteriophage may simply be mixed or suspended with the hydrogel.

The composition or matrix may, in an embodiment, be in a wet state and in the form of a hydrogel or a membrane.

In an embodiment, the composition or matrix in a wet state is in the form of a layer, a coating, a film, a sheet, or a membrane.

The composition or matrix may, for example, be a product comprising the composition or matrix in a wet state. Such a product may be a medical composition or product that may be intended for use, for example, in delivering a bacteriophage to a subject.

Such a composition, matrix or product may be sprayable; to that end, the composition, matrix or product may have a consistency that renders it suitable for being sprayed. For example, a consistency of up to 1.5% (w/w), or in the range of 0.1 to 1.5% (w/w), or in the range of 0.2 to 1% (w/w) may be suitable. Nanofibrillar cellulose hydrogels are highly shear-thinning, so they may be sprayable even at relatively high consistencies. Such a composition, matrix or product may be suitable for topical treatment, for example. It may be sprayed on a subject and into a thin layer containing the bacteriophage. Spraying the composition or matrix on a subject could be less painful for the subject than e.g. applying a patch or bandage. In other embodiments, the composition or matrix may, for example, be a hydrogel for topical, oral, sublingual, intraocular, intestinal, rectal, subcutaneous, parenteral or mucoadhesive application.

The composition or matrix may, in an embodiment, be in the form of a membrane.

Such a membrane may be prepared by wetting a membrane comprising nanofibrillar cellulose in a mixture of a bacteriophage and a buffer, for example saline. Such a membrane may also be formed e.g. by mixing or suspending the bacteriophage with nanofibrillar cellulose, e.g. with a nanofibrillar cellulose, forming a membrane of the mixture. Water may be removed from the mixture, if desired or necessary.

The membrane may contain e.g. 1-50% (w/w) of the nanofibrillar cellulose. The thickness of the membrane may be varied depending on e.g. the intended use. For example, the thickness of the membrane may be from 1 μm to 5 mm, 1 to 1000 μm, from 5 to 500 μm, or 50 to 300 μm. The thickness of the membrane forming a medical product or a part of a medical product, for example for wound healing purposes, may be about 10-100 μm. Such a membrane may be suitable for handling, storage, shipping etc. even in the absence of a solid support. In embodiments in which the membrane is arranged on a solid support, for example as a part of a multi-layer medical product, as a coating or layer, or on a solid support such as a multiwell plate, the thickness of the membrane might be only 1-5 μm thick. However, other thicknesses may also be contemplated.

In an embodiment, the composition or matrix is in a dry state.

The term "dry state" may, in the context of this specification, refer to a state in which the composition or matrix comprises water and/or an aqueous solution less than 10% (w/w). In other words, the moisture content of the composition or matrix in the dry state may be lower than 10% (w/w). However, a dry composition or matrix may still contain an amount of moisture, for example 1-10% (w/w), or 5-10% (w/w), or 1-5% (w/w).

The dry state may be achieved simply by e.g. air-drying a mixture of the bacteriophage and the nanofibrillar cellulose. Various drying procedures and/or means may alternatively or additionally be used. The temperature and other conditions during the drying may vary, although the conditions may be selected such that the viability of the bacteriophage is not reduced or significantly reduced.

However, the drying may work better for some bacteriophages than for others. For example, relatively small phages may tolerate the drying better than large ones.

In the dry state, the composition or matrix may be easier to handle, store, transport etc. Its volume may be reduced, and the risk of contamination from the composition or matrix may be reduced.

Such a composition or matrix in a dry state may be, for example, in the form of a membrane. Such a membrane may be obtainable e.g. by drying a composition or matrix in a wet state in the form of a membrane. Such a membrane may be suitable for handling, storage, shipping etc. even in the absence of a solid support.

In an embodiment, the composition or matrix in a dry state is in the form of a layer, a coating, a film, a sheet, or a membrane.

In an embodiment, the composition or matrix is in the form of spray-dried particles.

The composition or matrix may, additionally or alternatively, be a sprayable product, a combination product, an implant, a transdermal patch or a formulation for oral, sublingual, topical, intraocular, intestinal, rectal, subcutaneous, parenteral or mucoadhesive application.

The nanofibrillar cellulose may form a NFC matrix with interconnected pores within the composition or matrix. The bacteriophage may be at least partially present as bacteriophage particles in the matrix in a two- or three-dimensional arrangement. The bacteriophage particles may be homogeneously or heterogeneously distributed in the matrix. The distribution of the bacteriophage particles may depend e.g. on how thoroughly they are suspended or mixed in the composition or matrix. The bacteriophage particles have relatively small physical dimensions and are significantly smaller than e.g. mammalian cells, so they may be relatively easily distributed within the matrix. Similarly, they may be relatively easily released from the matrix. There may not be any need to use any specific procedures for breaking down the matrix to release the bacteriophage particles, although one may, in some embodiments, be employed.

The disintegrated fibrous cellulosic raw material may be modified or nonmodified fibrous raw material. Modified fibrous raw material means raw material where the fibers are affected by a modification treatment so that cellulose nanofibrils are more easily detachable from the fibers. The modification may be performed to fibrous cellulosic raw material which exists as a suspension in a liquid, e.g. pulp.

The modification treatment to the fibers may be chemical or physical. In chemical modification, the chemical structure of cellulose molecule is changed by a chemical reaction ("derivatization" of cellulose), for example so that the length of the cellulose molecule is not affected but functional groups are added to β-D-glucopyranose units of the polymer. The chemical modification of cellulose may take place at a certain conversion degree, which is dependent on the dosage of reactants and the reaction conditions, and often it is not complete so that the cellulose will stay in solid form as fibrils and does not dissolve in water. In physical modification, anionic or nonionic substances or any combination of these may be physically adsorbed on cellulose surface. The modification treatment may also be enzymatic. The cellulose in the fibers may be particularly ionically charged after the modification, because the ionic charge of the cellulose may weaken the internal bonds of the fibers and may later facilitate the disintegration to nanofibrillar cellulose. The ionic charge may be achieved by chemical or physical modification of the cellulose. The fibers may have a higher anionic charge after the modification compared with the starting raw material. Commonly used chemical modification methods for making an anionic charge may include oxidation, where hydroxyl groups are oxidized to aldehydes and carboxyl groups, sulphonization and carboxymethylation.

The cellulose may be oxidized. In the oxidation of cellulose, primary hydroxyl groups of cellulose may be oxidized catalytically by a heterocyclic nitroxyl compound, for example 2,2,6,6-tetramethylpiperidinyl-1-oxy free radical, generally called "TEMPO". At least some of the primary hydroxyl groups (C6-hydroxyl groups) of the cellulosic β-D-glucopyranose units may be selectively oxidized to carboxylic groups. Some aldehyde groups may also be formed from the primary hydroxyl groups. The cellulose may be oxidized to a level having a carboxylic acid content in the oxidized cellulose in the range of 0.6-1.4 mmol COOH/g pulp, or 0.8-1.2 mmol COOH/g pulp, for example to 1.0-1.2 mmol COOH g pulp, determined by conductometric titration. When the fibers of oxidized cellulose obtained in this manner are disintegrated in water, they may give a stable transparent dispersion of individualized cellulose fibrils, which may be, for example, of 3-5 nm in width.

In an embodiment, the nanofibrillar cellulose or a derivative thereof comprises or is native nanofibrillar cellulose. Native nanofibrillar cellulose appears well suited for bacteriophages.

The nanofibrillar cellulose or a derivative thereof may also be a mixture of native nanofibrillar cellulose and one or more other nanofibrillar cellulose types or grades.

In an embodiment, the nanofibrillar cellulose comprises chemically modified nanofibrillar cellulose, such as anionically modified nanofibrillar cellulose. In an embodiment, the nanofibrillar cellulose is anionically modified nanofibrillar cellulose. In an embodiment, the anionically modified nanofibrillar cellulose is oxidized nanofibrillar cellulose. In an embodiment, the anionically modified nanofibrillar cellulose is sulphonized nanofibrillar cellulose. In an embodiment, the anionically modified nanofibrillar cellulose is carboxymethylated nanofibrillar cellulose.

The composition or matrix may further comprise other components, for example a bioactive agent or a medicament. Such components may be mixed with the composition or matrix or incorporated in the matrix. The bioactive agent may be e.g. any one of the bioactive agents disclosed in WO 2013/072563 (e.g. p. 13, 1.5-p. 20, 1.2), which is herein incorporated in its entirety.

It may be beneficial if the composition or matrix does not contain any anti-infective agents or antibiotics. In an embodiment, the composition or matrix is neutral. In an embodiment, the pH of the composition or matrix is in the range of 5 to 9, or of 6 to 8.

An arrangement for storing, culturing, transporting and/or delivering a bacteriophage is disclosed. The arrangement comprises a solid support and a composition or matrix comprising nanofibrillar cellulose or a derivative thereof in a wet or dry state arranged on the solid support.

In the context of this arrangement, the composition or matrix may be any composition or matrix comprising nanofibrillar cellulose or a derivative thereof described in this specification. However, in this context, the composition or matrix does not necessarily include a bacteriophage—it may be added later for storage, culturing, transporting and/or delivery.

An arrangement is also disclosed, the arrangement comprising a solid support and the composition or matrix according to one or more embodiments disclosed in this specification arranged on the solid support.

Any features described below may be understood as relating to any one of the above arrangements.

The solid support of the arrangement may make the handling, shipping etc. of the composition or matrix easier. It may also facilitate further operations with the composition or matrix. For example, prokaryotic cell suspension may be added to the composition or matrix on the solid support. Then the prokaryotic cells on the arrangement may be allowed to grow and multiply, and the arrangement may be observed so as to determine whether the bacteriophage in the composition or matrix is capable of infecting the prokaryotic cells.

The shape, size and/or volume of the solid support is not particularly limited. For example, it may be a receptacle, such as a tube, a vial, a vessel, a syringe, or a bottle. Examples of such tubes and vials may be plastic tubes and vials of various shapes and sizes commercially available. Such tubes and vials may be provided e.g. with screw caps or snap caps. Examples may include 15 and 50 ml centrifuge tubes, Eppendorf tubes, 0.5 to 2 ml microcentrifuge tubes, etc. Further examples of receptacles may include e.g. a plate, such as a multiwell plate, a bioreactor, a scaffold, or a 3-D microfluidic culture chip.

The solid support, for example a receptacle, may have a recess, or a plurality of recesses, for receiving and/or containing the composition or matrix.

In other embodiments, the solid support may simply have an area on which the composition or matrix may be arranged.

In other embodiments, the composition or matrix may be impregnated in the solid support, for example to a gauze, as will be described below.

Multiwell plates, such as 6-, 12-, 24-, 48-, 96-, 384-, and 1536-well plates, may be commercially available and may be well suited as the solid support. Such multiwell plates may be made of various materials, such as plastic, for example polystyrene. The wells may have various different shapes, for example they may have a round or a flat bottom or a V-bottom.

In an embodiment, the composition or matrix is arranged on a plurality of locations on the solid support. Different bacteriophages may be added to the composition or matrix on individual locations. Or, in another embodiment, a plurality of compositions or matrices comprising different bacteriophages may be arranged in individual locations on the solid support.

In an embodiment, the solid support is a multiwell plate, and the composition or matrix is arranged in one or more wells of the multiwell plate. In such an arrangement, a plurality of compositions or matrices, each containing a bacteriophage, may be arranged in the wells of the multiwell plate, such that individual wells may contain different bacteriophages.

Such an arrangement may thus comprise, for example, a bacteriophage library. The arrangement may thus be well suited e.g. for transport and shipping a bacteriophage library, and/or for adding a prokaryotic cell suspension or a plurality of different prokaryotic cell suspensions to the individual composition(s) or matrix (matrices), for example for screening which one(s) of the bacteriophages is capable of infecting the prokaryotic cells in the suspension(s).

The solid support, for example a receptacle, may have a recess, or a plurality of recesses, for receiving and/or containing the composition(s) or matrix (matrices) and subsequently for receiving and/or containing a prokaryotic cell suspension and/or a plurality of different prokaryotic cells suspensions. In such an embodiment, the prokaryotic cells suspension(s) may be added directly to the solid support and to the composition(s) or matrix (matrices), such that the bacteriophage(s) in the composition(s) or matrix (matrices) may infect the prokaryotic cells.

The arrangement may be closable and optionally also sealable so as to prevent spreading and/or contamination by the bacteriophage(s). For example, a multiwell plate may be closable and optionally sealable so as to retain the bacteriophage(s) in the well(s) of the multiwell plate and to prevent it from contaminating other wells of the multiwell plate (cross-contamination). The arrangement may further comprise a cover for the solid support. For example, multiwell plates may be provided with a cover or a lid; such covers or lids may be suitably shaped so as to fit the edge of the well(s), for example to prevent cross-contamination. Various receptacles, such as tubes, bottles, vessels, or bioreactors may be provided with e.g. a cover, a lid, a cork, a plug, a cap, or other suitable means for closing the receptacle.

The composition may, in some embodiments, be in the form of a membrane or layer, either in a wet or a dry state.

The composition, matrix or arrangement may be a medical product.

In an embodiment, the arrangement is a medical multilayer product, the solid support is in the form of a layer, and the composition or matrix is arranged as a layer on the solid support or impregnated in the solid support.

The medical products described in this specification may be used in several applications. One specific field is medical applications, wherein the medical product may be applied on living tissue, such as skin. The medical product may be, for example, a patch, a dressing, a bandage, or a filter, or as described above, it may be in the form of a sprayable hydrogel. The medical product may also be a therapeutic product, such as a therapeutic patch containing a medicament. The surface of the the medical product comprising the composition or matrix may be intended for being in contact with skin during its use. In addition for being a well suited product for the delivery of a bacteriophage to a subject, for example to the skin of a subject, the surface of the composition or matrix comprising the nanofibrillar cellulose or the derivative thereof may provide beneficial effects when it is in direct contact with the skin of a subject. For example, it may promote the healing of a wound or other damage on skin; it may promote the delivery of the bacteriophage and/or other substances from the medical product to skin; or it may treat or control bacterial infection.

The solid support may, for example, comprise or be a layer of gauze.

The composition or matrix may be prepared by mixing the bacteriophage with the nanofibrillar cellulose or a derivative thereof. The layer of gauze may then be treated, for example impregnated, with the composition or matrix. This may be carried out by providing the composition or matrix in a basin or the like and immersing or dipping the gauze into the composition or matrix. The gauze may be kept in the composition or matrix for a time period suitable for allowing the composition or matrix to impregnate the gauze, and then the gauze may be removed from the composition or matrix. The term "impregnation" may, in the context of this specification, refer to a process wherein a gauze is filled or soaked throughout, or substantially throughout, with a composition or matrix comprising nanofibrillar cellulose. In the impregnation the gauze may be filled, imbued, permeated or saturated with the composition or matrix, either partially or completely. The wet gauze may then be pressed to remove excess composition or matrix and liquid and to facilitate the penetration of the composition or matrix into the structure of the gauze. The gauze may be any suitable gauze, such as a fabric, a cloth or a similar material comprising fibers. The gauze may be woven or nonwoven, sterile or nonsterile, plain or impregnated, or fenestrated (perforated or with slits), or a combination thereof. The gauze may be provided as a gauze sheet or fabric, or as a similar structure. Such a medical product and a method for preparing it is described e.g. in WO 2017/174874, which is herein incorporated in its entirety.

Various other solid supports and materials for the solid support may be contemplated. Various synthetic polymers, bio compounds and natural polymers may be suitable. Examples of suitable materials may be e.g. the support materials described in WO 2013/072563 (p. 25, 1.12-p. 26, 1.19), which is herein incorporated in its entirety.

It may be beneficial if the composition or matrix or the arrangement does not contain any anti-infective agents or antibiotics. In an embodiment, the composition or matrix is neutral. In an embodiment, the pH of the composition or matrix is in the range of 5 to 9, or of 6 to 8.

The composition, matrix or arrangement may, additionally or alternatively, be a medical device, a combination product, an implant, a transdermal patch or a formulation for oral, sublingual, topical, intraocular, intestinal, rectal, subcutaneous, parenteral or mucoadhesive application.

A method for storing, culturing, transporting and/or delivering a bacteriophage is disclosed. The method may comprise mixing the bacteriophage with nanofibrillar cellulose or a derivative thereof, thereby obtaining a composition or matrix comprising the bacteriophage and the nanofibrillar cellulose or the derivative thereof.

For culturing the bacteriophage, prokaryotic cells suitable for the bacteriophage may be added to the composition or matrix. Suitable prokaryotic cells may be prokaryotic cells which the bacteriophage is capable of infecting and in which they are capable of multiplying.

The composition or matrix may be arranged on a solid support. The solid support may be any solid support described in this specification.

In an embodiment, the composition or matrix is arranged on a plurality of locations on the solid support. Different bacteriophages may be added to the composition or matrix on individual locations. Or, in another embodiment, a plurality of compositions or matrices comprising different bacteriophages may be arranged in individual locations. In an embodiment, the solid support is a multiwell plate, and the composition or matrix is arranged in one or more wells of the multiwell plate. In such an arrangement, a plurality of compositions or matrices, each containing a bacteriophage, may be arranged in the wells of the multiwell plate, such that individual wells may contain different bacteriophages. The method may thus be suitable for storing, culturing, transporting and/or delivering a bacteriophage library.

Such an arrangement may thus comprise, for example, a bacteriophage library.

The method may further comprise adding a prokaryotic cell suspension or a plurality of different bacterial suspensions to the individual composition(s) or matrix (matrices). This may allow for screening which one of the bacteriophages is capable of infecting the prokaryotic cells in the suspension(s).

The method may further comprise drying the composition or matrix. The drying may be done e.g. by air-drying, i.e. allowing the composition or matrix to air dry. The temperature and other conditions during the drying may vary, although the conditions may be selected such that the viability of the bacteriophage is not reduced or significantly reduced. For example, the drying may be done at room temperature, but lower or higher temperatures may also be used, depending e.g. on the bacteriophage. The time period required for the drying may depend e.g. on the consistency of the composition or matrix, its volume, the conditions etc. For a relatively small volume, such as 10 µl, drying for 2 hours or more at room temperature may be sufficient.

The method may further comprise one or more of the following:
  storing the composition or matrix;
  culturing the bacteriophage;
  transporting the composition or matrix; and/or
  delivering the bacteriophage from the composition or matrix to a destination or to a subject. The destination may be e.g. a prokaryotic cell culture.

The composition or matrix may, for example, be stored at room temperature or at ambient temperature, at 0 to 10° C., or at 2 to 8° C. Storage at a temperature lower than room temperature, such as at 4° C., may preserve phage viability better than storage at higher temperatures, such as room temperature. In the context of this specification, "room temperature" may refer to a temperature in the range of 18 to 25° C., for example of 20 to 22° C.

A method for preparing the composition or matrix according to one or more embodiments described in this specification or the arrangement according to one or more embodiments described in this specification is disclosed. The method may comprise mixing a bacteriophage with nanofibrillar cellulose or a derivative thereof. A composition or matrix comprising the bacteriophage and the nanofibrillar cellulose or the derivative thereof may thereby be obtained.

The composition or matrix may be arranged on a solid support. The solid support may be any solid support described in this specification.

In an embodiment, the composition or matrix is arranged on a plurality of locations on the solid support. Different bacteriophages may be added to the composition or matrix on individual locations. Or, in another embodiment, a plurality of compositions or matrices comprising different bacteriophages may be arranged in individual locations. In an embodiment, the solid support is a multiwell plate, and the composition or matrix is arranged in one or more wells of the multiwell plate. In such an arrangement, a plurality of compositions or matrices, each containing a bacteriophage, may be arranged in the wells of the multiwell plate, such that individual wells may contain different bacteriophages. Such an arrangement may thus comprise, for example, a bacteriophage library.

The method may further comprise drying the composition or matrix.

A method for multiplying a bacteriophage and/or testing the ability of a bacteriophage to infect prokaryotic cells is also disclosed. The method may comprise adding prokaryotic cells to the composition or matrix according to one or more embodiments described in this specification or to the composition or matrix of the arrangement according to one or more embodiments described in this specification, and maintaining the composition, matrix or arrangement in conditions suitable for culturing the prokaryotic cells, thereby allowing the bacteriophage to infect the prokaryotic cells.

The prokaryotic cells may comprise or be bacteria and/or archaea.

Use of a composition or matrix comprising nanofibrillar cellulose or a derivative thereof in a wet or dry state for storing, culturing, transporting and/or delivering a bacteriophage is disclosed.

The composition or matrix according to one or more embodiments described in this specification or of the arrangement according to one or more embodiments described in this specification for use in therapy is disclosed.

The composition or matrix according to one or more embodiments described in this specification or of the arrangement according to one or more embodiments described in this specification for use in the treatment of damage, an injury, a disease or a disorder of a tissue, such as skin, is disclosed. Such damage or injury of skin may include e.g. an open or closed wound.

The composition or matrix according to one or more embodiments described in this specification or of the arrangement according to one or more embodiments described in this specification for use in the treatment of a bacterial infection is disclosed.

Use of the composition or matrix according to one or more embodiments described in this specification or of the arrangement according to one or more embodiments described in this specification in therapy is disclosed.

Use of the composition or matrix according to one or more embodiments described in this specification or of the arrangement according to one or more embodiments described in this specification in the treatment of damage, an injury, a disease or a disorder of a tissue, or a bacterial infection is disclosed.

It should be understood that in the context of any one of the methods and uses described above, the composition or matrix, the arrangement, and the bacteriophage may be any composition or matrix, arrangement, or bacteriophage described in this specification, including any specific embodiments described in this specification.

EXAMPLES

Reference will now be made in detail to various embodiments, an example of which is illustrated in the accompanying drawing.

The description below discloses some embodiments in such a detail that a person skilled in the art is able to utilize the embodiments based on the disclosure. Not all steps or features of the embodiments are discussed in detail, as many of the steps or features will be obvious for the person skilled in the art based on this specification.

Example 1—Materials

In the following examples, the term "GrowDex" or "GrowDex®" refers to nanofibrillar cellulose hydrogel. The GrowDex used in these examples is native nanofibrillar cellulose hydrogel.

Native NFC (GrowDex®) was made from bleached cellulose pulp by high pressure homogenization using industrial fluidizer for fibrillation. The raw material was aseptically collected from a pulp mill and thoroughly purified prior to the homogenization with sterilized machinery. Thus, the microbial purity was maintained through the whole production process. The purified pulp fibers were diluted with sterilized, ultra high quality water before the fibrillation. The nanofiber hydrogel was autoclaved (121° C./20 min) directly after fibrillation. The consistency of the GrowDex used in the experiments was 1.5% (w/w).

The bacteriophages used in the experiments were the following:

fRuSau02 (full name vB_SauM_fRuSau02; described in Leskinen et. al. Viruses 2017, 9, 258; doi:10.3390/v9090258)

ΦEBHT. Source: DSMZ, Germany (Leibniz Institute DSMZ-German Collection of Microorganisms and Cell Cultures)

fHoEco02 (full name vB_EcoM_fHoEco02; Kiljunen et al. 2018, Genome Announc 6:e00401-18; https://doi.org/10.1128/genomeA.00401-18)

fTu-Eco01 (not published, from the collection of the present inventors, isolated from sewage)

Bacteriophages and the compositions or matrices used in the experiments were diluted in SM buffer or in 0.9% NaCl when necessary. The following bacteriophages were used for the following bacteria:

*S. aureus* 13KP (#5676): the host for fRuSau02

*S. aureus* 19A2 (#6433); the host for ΦEBHT

*E. coli* 123738 (#5521), the host for fHoEco02

*E. coli* 123789 (#5507), the host for fTu-Eco01

Other bacterial strains are isolated from patients, source HUSLab, but 19A2 was isolated from healthy pig by Annamari Heikinheimo, The Faculty of Veterinary Medicine, University of Helsinki.

Example 2—Effect of NFC Hydrogel on Bacterial Growth

NFC hydrogel was diluted with either SM buffer or 0.9% NaCl to consistencies of 0 (control), 0.1, 0.5, 1.0 and 1.5% (w/w). 10 μl drops of the dilutions were aliquoted onto wells of 96-well plate. 200 μl of diluted overnight culture of bacteria (*Escherichia coli* strains 123738 (#5521) and 123789 (#5507) and *Staphylococcus aureus* strains 13KP (#5675) and 19A2 (#6433) were added on the wells. Bacterial growth was monitored by following OD600 for five hours. FIG. 1 shows exemplary results for *E. coli* 123789 (#5507).

All tested bacteria were found to grow equally well in all GrowDex consistencies and in both buffers used as NFC diluent. This illustrates that NCF hydrogel in the consistencies used does not inhibit bacterial growth.

Example 3—Effect of NFC Hydrogel on Bacteriophage Viability in Spot Test

The bacteriophages were diluted 1:100 with either SM buffer or 0.9% NaCl and both phage dilutions were mixed with GrowDex hydrogels with consistencies of 0.1, 0.5, 1.0 and 1.5% (w/w). Phages stored in SM buffer and 0.9% NaCl were used as controls. The compositions obtained were stored for approx. 2 h at 4° C. The compositions were diluted in SM buffer or in 0.9% NaCl, respectively, as serial dilutions ($10^{-4}$, $10^{-5}$, $10^{-6}$ and $10^{-7}$). Drops of the diluted compositions were placed on lawns of the bacteria grown on agar in Petri dishes. The ability of the phages to infect the bacteria were observed.

Figure 2:
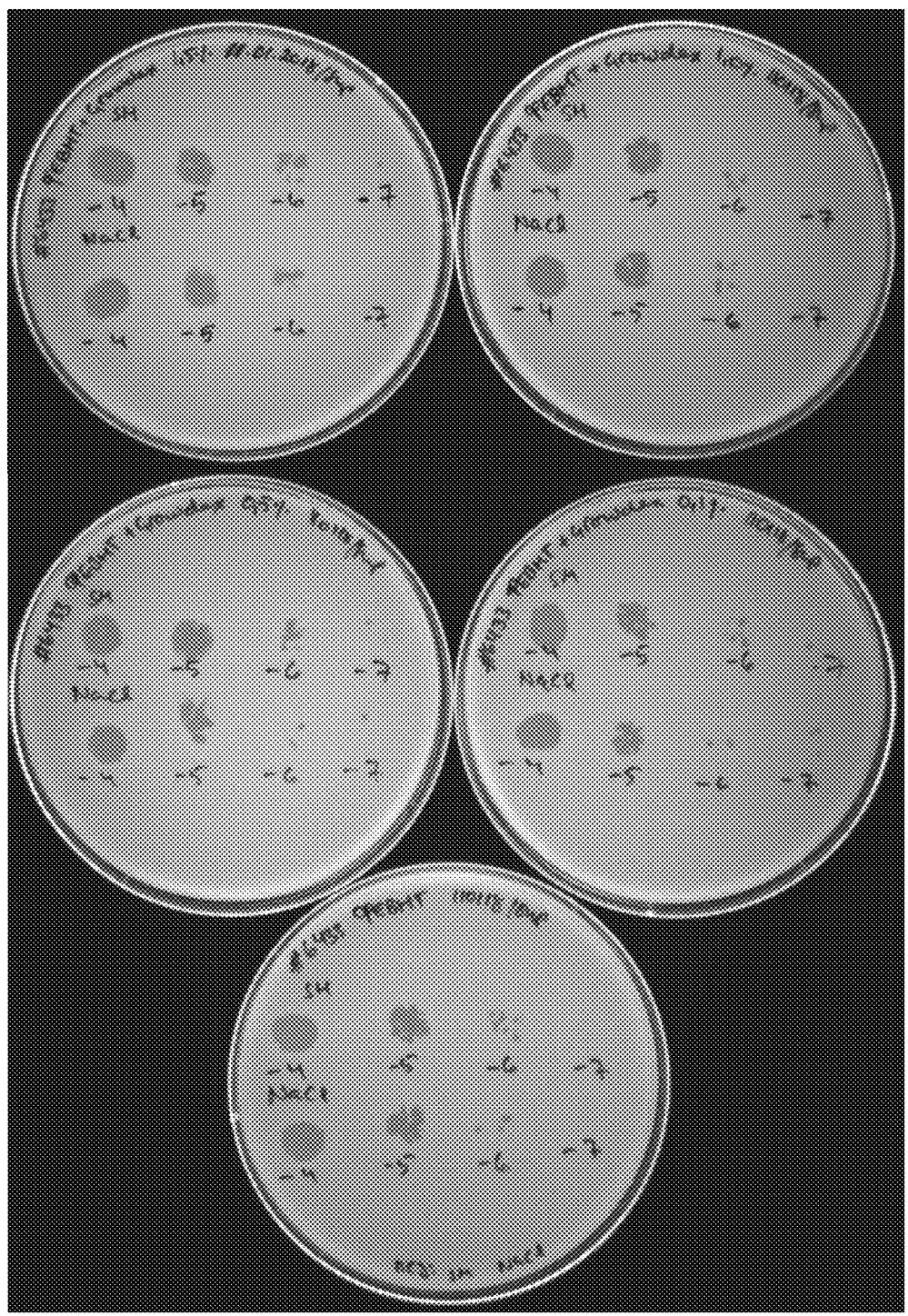
FIG. 2 shows exemplary results for ΦEBHT stored in GrowDex® in *S. aureus* strain 19A2 (#6433)

The dilutions of the compositions containing GrowDex were found to be as viable as the dilutions of the phages stored in SM buffer or 0.9% NaCl. FIG. 2 shows exemplary results for ΦEBHT in *S. aureus* strain 19A2 (#6433). Therefore, the phages were found to be well released from the GrowDex matrix upon dilution and capable of infecting the bacteria. The specificity of the phages to the bacteria was not affected by the presence of GrowDex. In addition, phage viability was not dependent on whether SM buffer or 0.9% NaCl was used as diluent.

Example 4—Effect of NFC Hydrogel on Bacteriophage Viability in Liquid Assay

Figure 3:
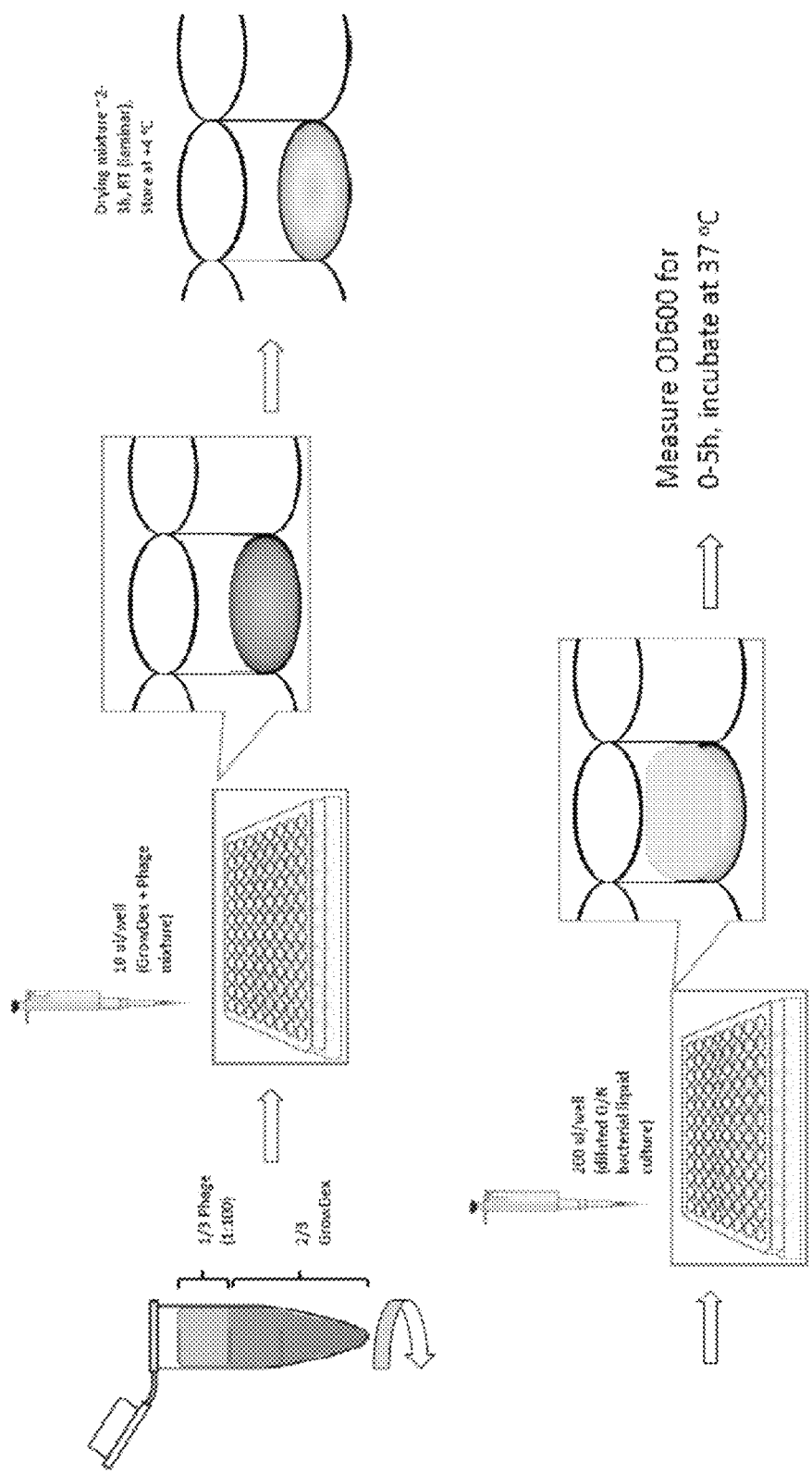
FIG. 3 shows a schematic representation of the experimental setup.

A schematic of the experimental setup is shown in FIG. 3.

Phage dilutions (1:100) were mixed with GrowDex (1%, 0.5% or 0.1%) or with SM buffer (control) at a volume ratio of 1:2. 10 µl of each mixture (composition/matrix) was pipetted to a well of a multiwell plate and either stored as such (wet GrowDex) or allowed to air dry for 2-3 h at room temperature in a laminar. After storage of the plate with wet composition/matrix or the dried plate for approx. 2 h at 4° C., 200 µl of diluted bacterial liquid culture was added to the compositions/matrices in each well. The effect of the phages to the bacterial culture was observed by incubating the plate at 37° C. and by measuring OD600 in each well during a period of 0-5 h.

Figure 4:
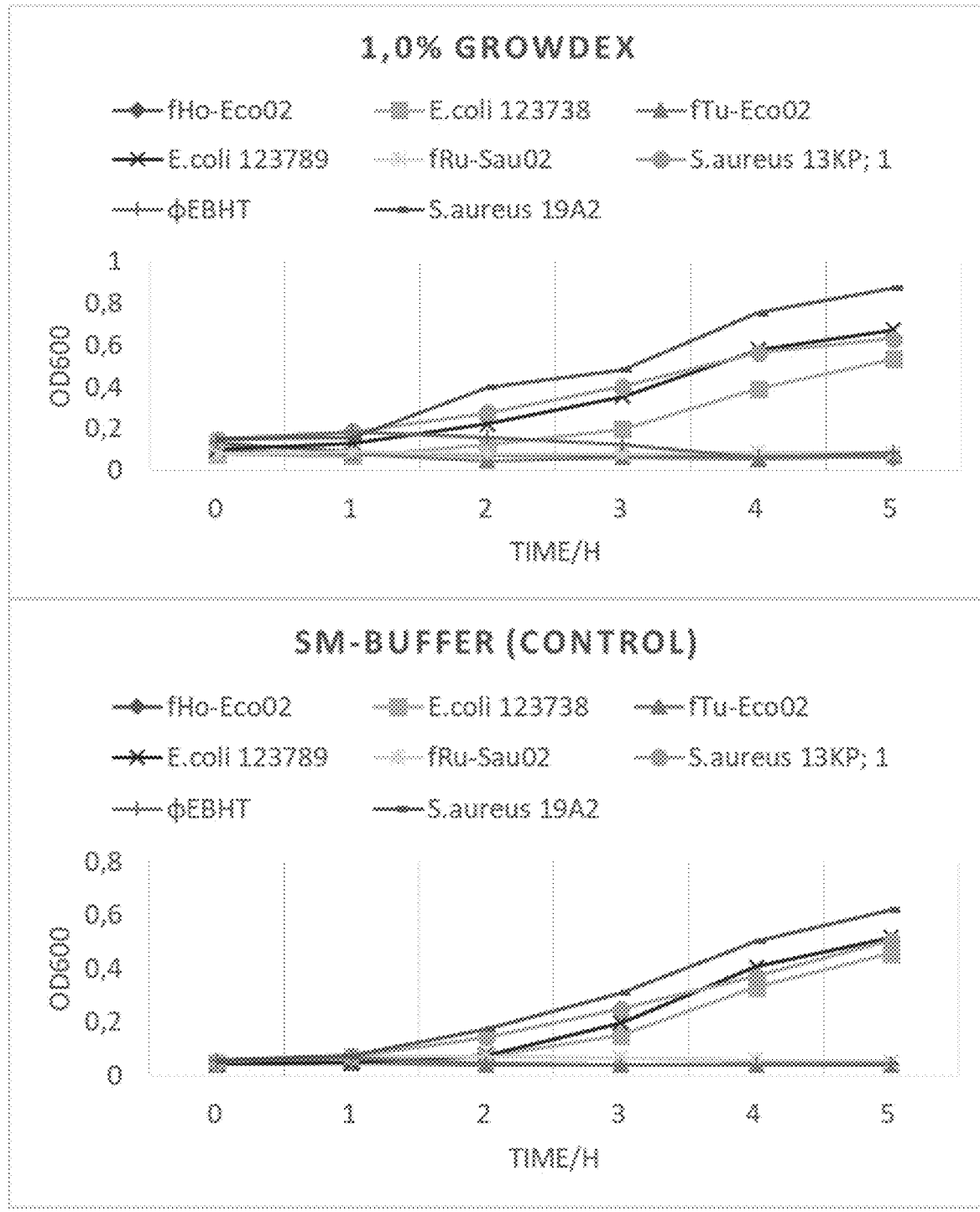
FIG. 4 illustrates the effects of storage in wet 1% GrowDex and SM buffer on the viabilities of different bacteriophages.

Results for wet 1% GrowDex and SM buffer are shown in FIG. 4. Bacteria without phages grew well and reached OD600 of ~0.5-0.7 within 5 h, but there was no visible bacterial growth in wells where bacteriophage was added. This illustrates that phages retain their infectivity in the conditions used and are released from NFC hydrogel when bacterial culture is added.

Similar results were observed in wet GrowDex at different consistencies.

Figure 5:
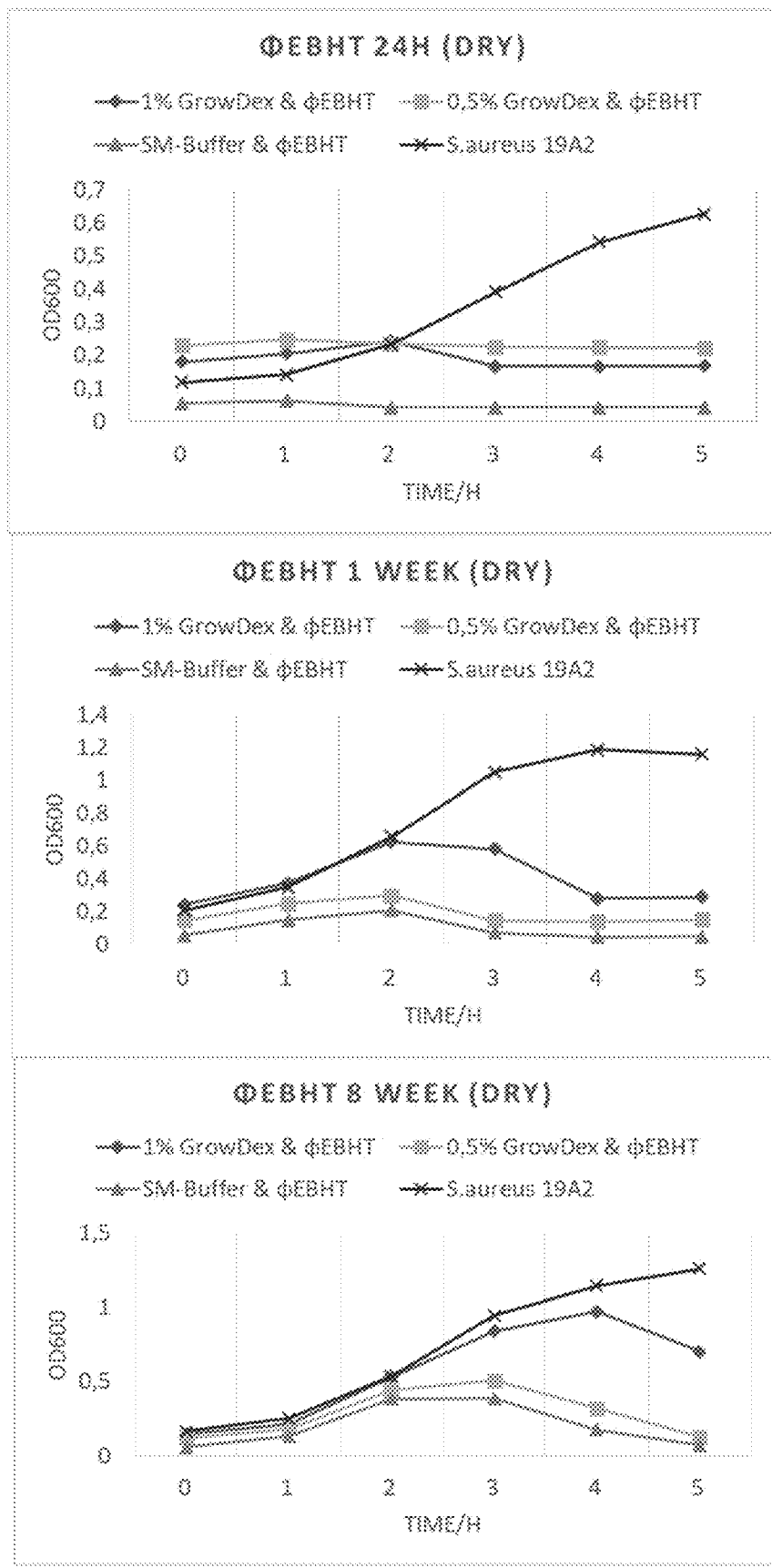
FIG. 5 shows exemplary results for ΦEBHT infecting *S. aureus* strain 19A2 stored in dry GrowDex®.

Example 5—Effect of Drying the Phage-NFC Hydrogel Mixture on Bacteriophage Viability The effect of of drying the phage-NFC hydrogel mixture was tested on multiwell plates in otherwise similar manner as in Example 4, but the 10 µl drops were allowed to air-dry in a biosafety cabinet at RT for 2 h prior to storing the plate at 4° C. Exemplary results for ΦEBHT infecting *S. aureus* strain 19A2 are shown in FIG. 5. After 24 h storage, the phage was able to inhibit bacterial growth completely. After 1 week and 8 week storage, the growth inhibition was less clear with phages stored in 1% NFC but still evident with phages in 0.5% composition and in SM buffer. However, different phages tolerate drying differently, and some phages may be inactivated in the process.

Example 6—Effect of Prolonged Storage on Bacteriophage Viability

The effect of prolonged storage was tested on multiwell plates in a similar manner as in Example 4. GrowDex concentrations of 1.0%, 0.5% and 0% were used, and dilutions were made in SM Buffer. The compositions/matrices were stored as follows:

Wet pellet (10 µl in 96-well plate, covered with foil/plastic shield)

Liquid form (stored in 2 ml microcentrifuge tube)

Each arrangement was stored for 24 h, 1 week, 2, 4, 8 weeks or 6 months. Again, bacterial culture was added thereto, and OD600 was measured for 0-5 h.

Figure 6:
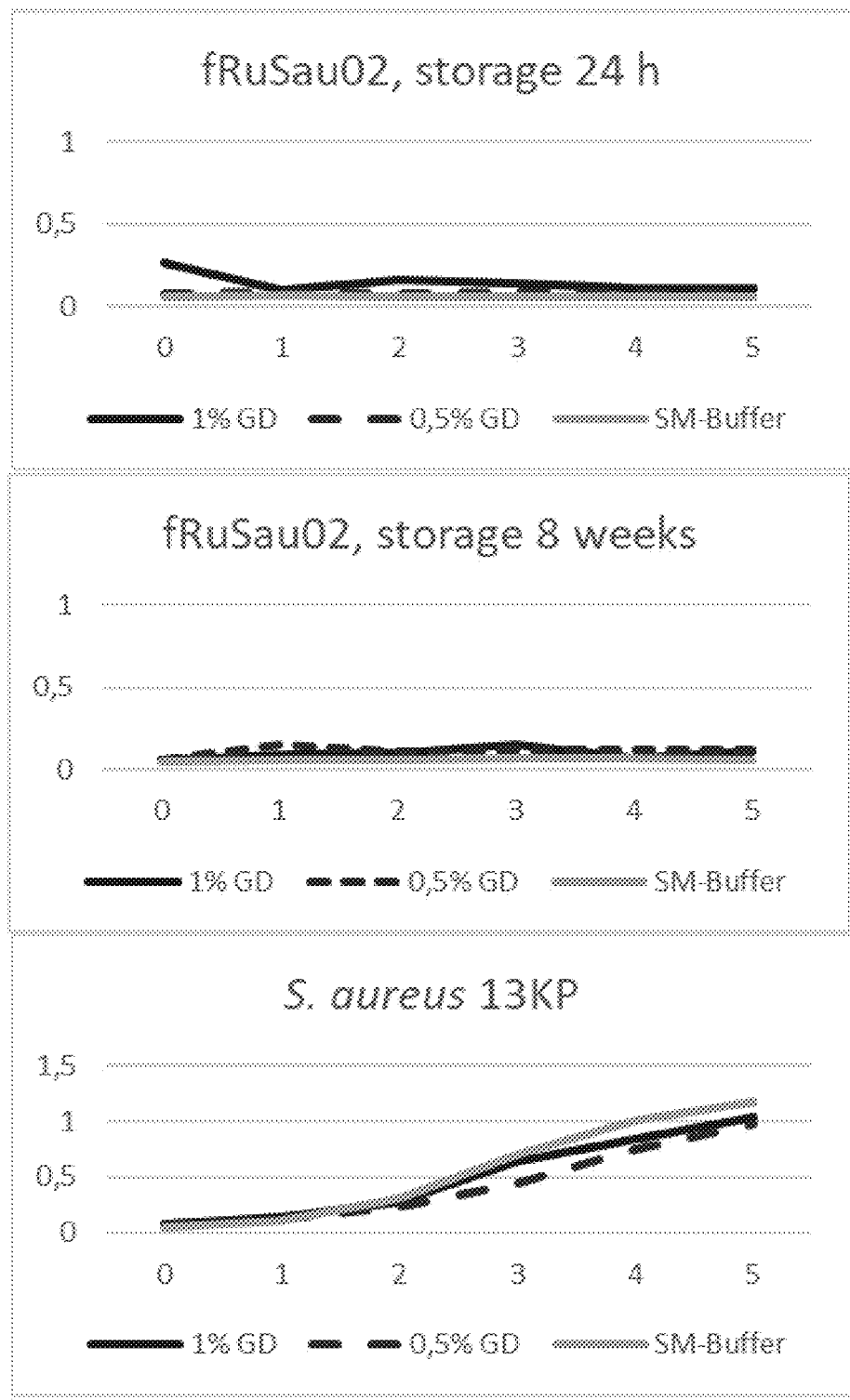
FIG. 6 shows exemplary results for fRuSau02 stored in 1% and 0.5% NFC and in SM buffer for 24 h and 8 weeks.

All phages tested maintained their viability well in GrowDex. In 6 months time point, 10 µl drops stored on plates had dried and big myoviruses (fHoEco02 and fRuSau02) lost their infectivity. However, even in this time point, all the phages stored in 2 ml tubes were fully infectious. Exemplary results for fRuSau02 stored in 1% and 0.5% NFC and in SM buffer for 24 h and 8 weeks are shown in FIG. 6. As a control, the growth of the host bacterium *S. aureus* 13KP without the phage is shown.

Example 7—Shipping Test

A multiwell plate prepared as described above (1% GrowDex, 4 test phages (2 phages specific for *S. aureus,* 2 specific for *E. coli*) was sent by mail, such that the transport took approx. 3 days. Measurements were made 7 days later. During the transport and storage, the plate was stored partially at room temperature, +4° C., and −15° C.

Figure 7:
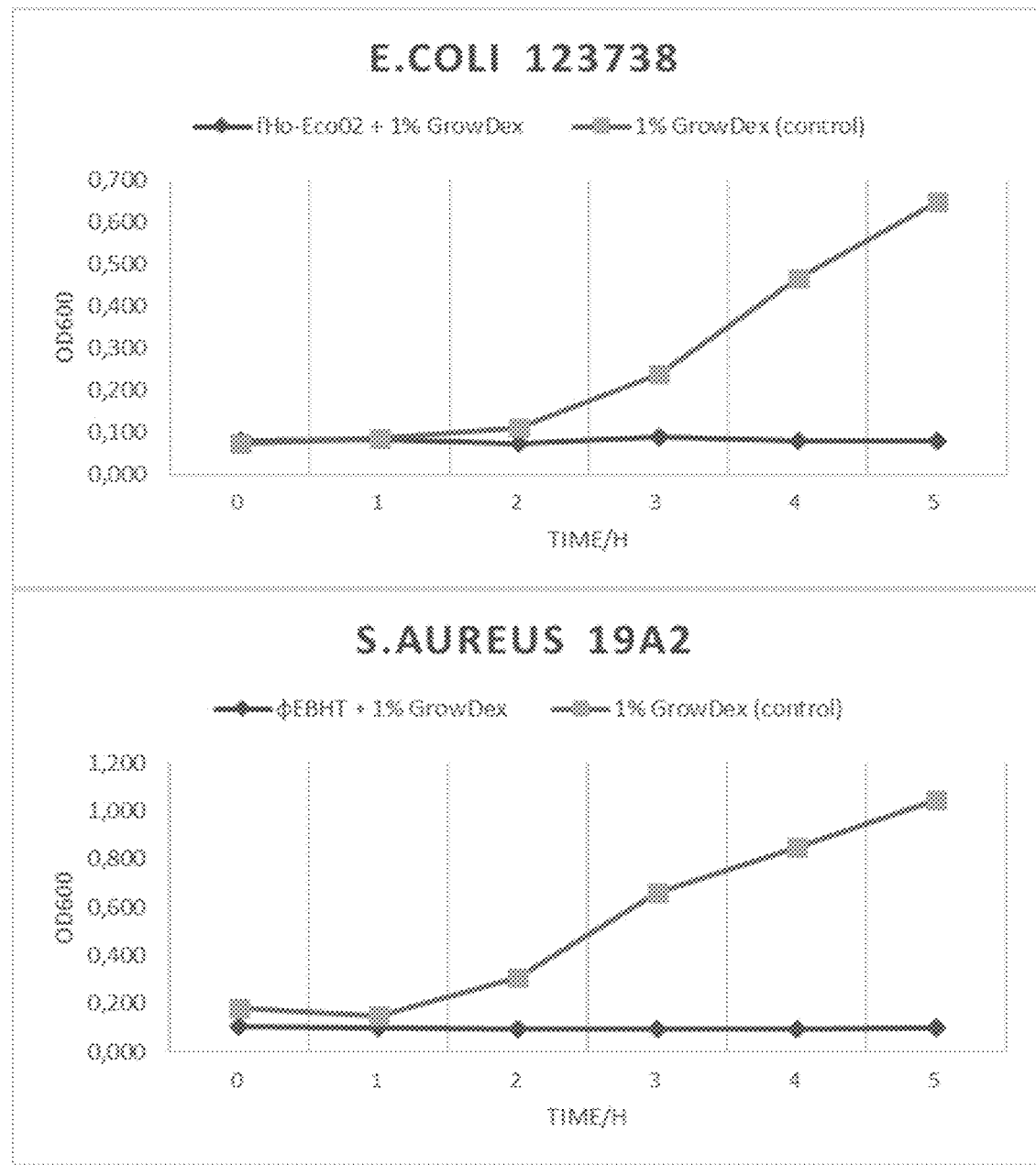
FIG. 7 illustrates the results of the shipping test for fHoEco02 in *E. coli* 123738 (#5521) and ΦEBHT in *S. aureus* 19A2 (#6433)

The viability of the phages was tested as described above. All test phages were found to be fully infectious. Results for fHoEco02 in *E. coli* 123738 (#5521) and ΦEBHT in *S. aureus* 19A2 (#6433) are shown in FIG. 7.

Figure 8:
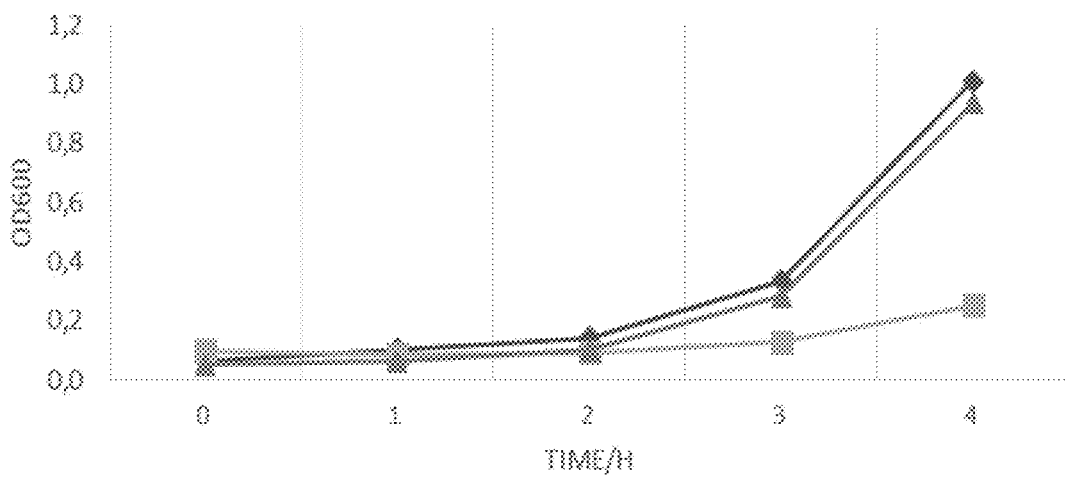
FIG. 8 shows the effect of other commercial hydrogels on bacterial growth.
Figure 8:
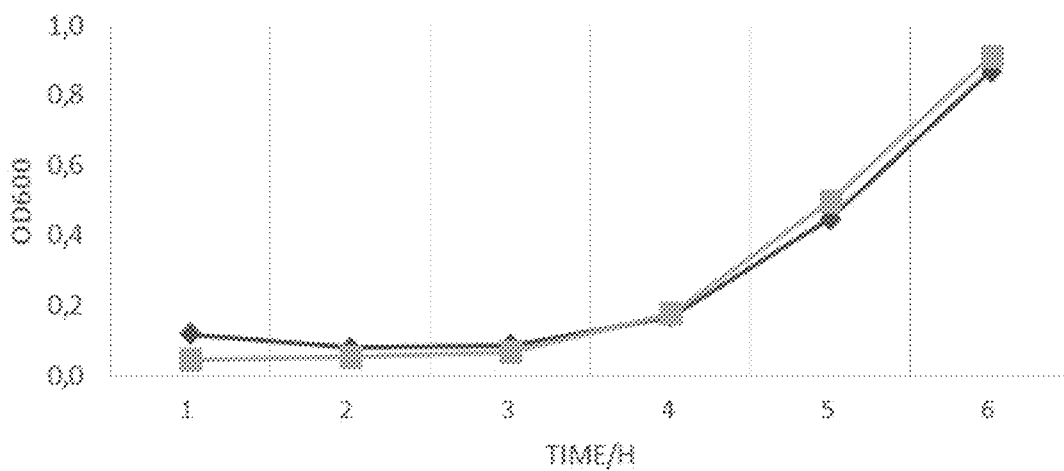

Example 8—Effects of Commercial Hydrogels on Bacterial Growth and Bacteriophage Viability The effect of three different hydrogels (GROWDEX® hydrogel, INTRASITE® hydrogel from T. J. Smith and Nephew, England, and PURILON® hydrogel from Coloplast A/S, Denmark) was tested on multiwell plates in a similar manner as in Example 2. Exemplary results for *S. aureus* strain 13KP are shown in FIG. 8. GROWDEX® hydrogel and INTRASITE® hydrogel did not affect bacterial growth, but PURILON® hydrogel showed clear growth inhibition. Similar results were obtained with all the four tested bacterial strains.

Figure 9:
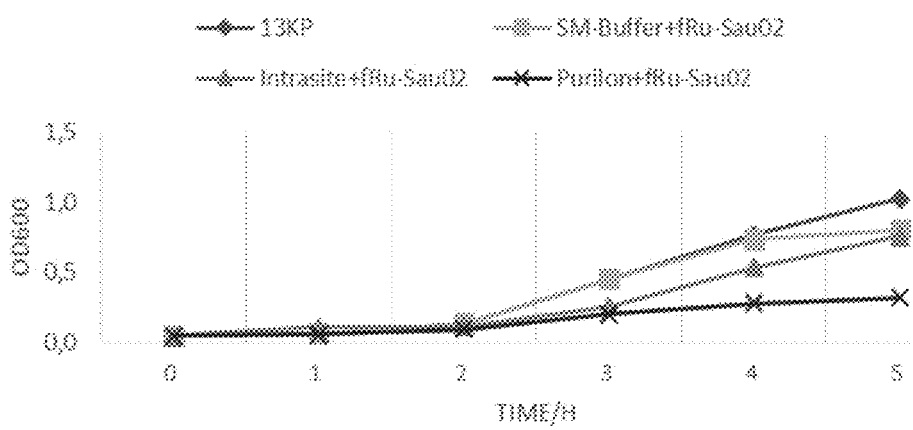
FIG. 9 shows exemplary results for fRuSau02 infecting *S. aureus* strain 13KP stored in other commercial hydrogels and in GrowDex®.
Figure 9:
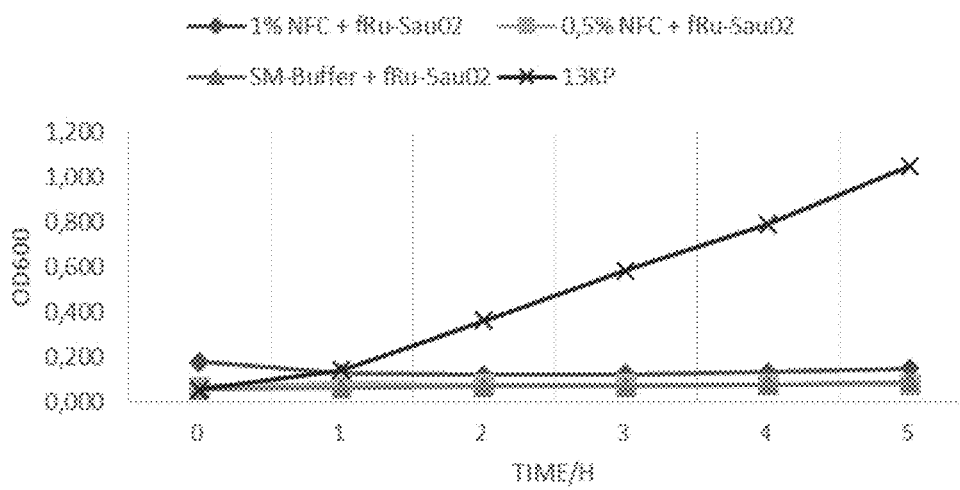

The effect of hydrogels on bacteriophage viability in liquid assay was tested in a similar manner as in Example 4. Multiwell plates with phage and GrowDex were stored at 4° C. and phage with other two gels (Intrasite and Purilon) at RT, as recommended by their manufacturers. The storage time prior to phage viability test was one week. Exemplary results for fRuSau02 infecting *S. aureus* strain 13KP are shown in FIG. 9. After 1 week of storage, phage stored at 4°

C. in NFC (1% and 0.5%) were fully infectious and inhibited bacterial growth completely. However, phages stored at RT in the other gels had lost their infectivity. The figure shows a growth inhibition of 13KP by Purilon gel, but this inhibition is probably due to the gel itself and not the phage as mentioned above.

It is obvious to a person skilled in the art that with the advancement of technology, the basic idea may be implemented in various ways. The embodiments are thus not limited to the examples described above; instead they may vary within the scope of the claims.

The embodiments described hereinbefore may be used in any combination with each other. Several of the embodiments may be combined together to form a further embodiment. A method, a product, a system, or a use, disclosed herein, may comprise at least one of the embodiments described hereinbefore. It will be understood that the benefits and advantages described above may relate to one embodiment or may relate to several embodiments. The embodiments are not limited to those that solve any or all of the stated problems or those that have any or all of the stated benefits and advantages. It will further be understood that reference to 'an' item refers to one or more of those items. The term "comprising" is used in this specification to mean including the feature(s) or act(s) followed thereafter, without excluding the presence of one or more additional features or acts.

The invention claimed is:

1. A composition or matrix comprising:
a bacteriophage mixed or suspended in nanofibrillar cellulose or a derivative thereof, wherein the bacteriophage is viable and wherein the nanofibrillar cellulose comprises fibrils having a high aspect ratio, a length exceeding 1 µm, and a diameter smaller than 200 nm, the nanofibrillar cellulose providing a zero shear viscosity in the range of 1000-100000 Pa·s and a yield stress in the range of 1-50 Pa,
the composition or matrix being in a wet state wherein the composition or matrix is in the form of a hydrogel with a nanocellulose consistency of 0.1-1.5% (w/w), or
the composition or matrix being in a dry state, wherein the moisture content of the composition or matrix is lower than 10% (w/w).

2. The composition or matrix according to claim 1, wherein the composition or matrix is in a wet state and in the form of a hydrogel.

3. The composition or matrix according to claim 1, wherein the composition or matrix is in a dry state.

4. The composition or matrix according to claim 1, wherein the bacteriophage is at least partially present as bacteriophage particles in the matrix in a two- or three-dimensional arrangement.

5. The composition or matrix according to claim 1, wherein the nanofibrillar cellulose or a derivative thereof comprises or is native nanofibrillar cellulose.

6. An arrangement comprising a solid support and the composition or matrix according to claim 1 arranged on the solid support.

7. The arrangement according to claim 6, wherein the solid support is a multiwell plate, and the composition or matrix is arranged in one or more wells of the multiwell plate.

8. The arrangement according to claim 6, wherein the arrangement is a medical multi-layer product, the solid support is in the form of a layer, and the composition or matrix is arranged as a layer on the solid support or impregnated in the solid support.

9. The composition or matrix according to claim 1 for use in therapy.

10. The composition or matrix according to claim 3, wherein the composition or matrix is in the form of a membrane.

11. The composition or matrix of claim 1, wherein the nanofibrillar cellulose is obtained from wood pulp or from hardwood pulp.

* * * * *